(12) United States Patent  
Christy

(10) Patent No.: US 8,754,369 B2  
(45) Date of Patent: Jun. 17, 2014

(54) SYSTEM AND METHOD FOR MEASURING HYDROGEN CONTENT IN A SAMPLE

(75) Inventor: Carlton N. Christy, Normandy Park, WA (US)

(73) Assignee: The Boeing Company, Chicago, IL (US)

(*) Notice: Subject to any disclaimer, the term of this patent is extended or adjusted under 35 U.S.C. 154(b) by 103 days.

(21) Appl. No.: 13/487,481

(22) Filed: Jun. 4, 2012

(65) Prior Publication Data  
US 2013/0320206 A1 Dec. 5, 2013

(51) Int. Cl.  
*G01N 7/16* (2006.01)  
*H01J 49/04* (2006.01)

(52) U.S. Cl.  
CPC .................. *H01J 49/049* (2013.01)  
USPC ....................................................... 250/288

(58) Field of Classification Search  
USPC ....................................................... 250/288  
See application file for complete search history.

(56) References Cited

U.S. PATENT DOCUMENTS

| | | | | |
|---|---|---|---|---|
| 4,142,399 A | * | 3/1979 | Sato et al. | 73/19.07 |
| 4,192,175 A | * | 3/1980 | Godai et al. | 73/19.02 |
| 4,660,297 A | * | 4/1987 | Danielson | 34/275 |
| 5,142,143 A | * | 8/1992 | Fite et al. | 250/288 |

OTHER PUBLICATIONS

European Search Report, EP 13 17 0496 (2013).  
Mizuno et al., "Determination of hydrogen concentration in austenitic stainless steels by thermal desorption spectroscopy," *Materials Transactions*, vol. 35, No. 10, pp. 703-707 (1994).  
Database WPI, Week 201019, Thomson Scientific, London, GB, AN 2010-C60115 & JP 2010 054498 A (Denshi Kagaku KK) (2010).  
Bergers et al., "Determination of Hydrogen in Steel by Thermal Desorption Mass Spectrometry," Steel Research Verlag Stahleisen GMBH Germany, vol. 81, No. 7, pp. 499-507 (2010).  
Das, K.B., "An Ultrasensitive Hydrogen Detector," *Hydrogen Embrittlement Testing, ASTM STP 543*, American Society for Testing and Materials, 1974, pp. 106-123.

* cited by examiner

*Primary Examiner* — Michael Logie  
*Assistant Examiner* — Eliza Osenbaugh-Stewar  
(74) *Attorney, Agent, or Firm* — Walters & Wasylyna LLC

(57) ABSTRACT

A measuring method including the steps of providing a chamber, drawing a vacuum in the chamber, placing a sample into the chamber, heating the sample to desorb a target species from the sample, passing a carrier gas through the chamber, the carrier gas mixing with the desorbed target species to form a mixture, and analyzing the mixture.

18 Claims, 3 Drawing Sheets

SYSTEM AND METHOD FOR MEASURING HYDROGEN CONTENT IN A SAMPLE

FIELD

This application relates to the measurement of the content of a particular species in a sample and, more particularly, to the measurement of hydrogen content in high-strength structural materials, such as high-strength steels and titanium alloys, for the evaluation of hydrogen embrittlement potential.

BACKGROUND

Structural aircraft components, such as landing gear, are subjected to significant stresses while in use. Therefore, structural aircraft components are typically constructed from high-strength structural materials, such as high-strength steels and titanium alloys. To inhibit environmental corrosion, high-strength steels are typically plated with a corrosion-resistant coating. Typical corrosion-resistant coatings include titanium-cadmium coatings and zinc-nickel coatings.

It has long been known that hydrogen diffuses through high-strength structural materials, thereby resulting in hydrogen embrittlement (i.e., the hydrogen-induced reduction in ductility that renders materials relatively more brittle than materials that have not been exposed to hydrogen). The process of plating high-strength structural materials with corrosion-resistant coatings has been known to significantly contribute to hydrogen embrittlement due to the evolution of hydrogen that occurs at the plating cathode.

Thus, prior to being deployed, high-strength structural materials are typically evaluated for hydrogen embrittlement. For example, ASTM F326 is a standard test method for the electronic measurement of hydrogen embrittlement potential resulting from cadmium electroplating processes. However, the ASTM F326 standard test method is not suitable for measuring hydrogen embrittlement potential resulting from zinc-nickel electroplating processes. As another example, ASTM F519 is a standard test method for the mechanical measurement of hydrogen embrittlement potential resulting from various electroplating processes. However, the ASTM F519 standard test method requires over 200 hours and, therefore, significantly increases overall production time.

Accordingly, those skilled in the art continue with research and development efforts in the field of hydrogen detection.

SUMMARY

In one embodiment, the disclosed measuring method may include the steps of (1) providing a chamber, (2) drawing a vacuum in the chamber, (3) placing a sample into the chamber, (4) heating the sample to desorb a target species from the sample, (5) passing a carrier gas through the chamber, the carrier gas mixing with the desorbed target species to form a mixture, and (6) analyzing the mixture.

In another embodiment, the disclosed measuring method may include the steps of (1) providing a chamber, (2) drawing a vacuum in the chamber, (3) placing a sample into the chamber, (4) heating the sample to desorb hydrogen from the sample, (5) passing a carrier gas through the chamber, the carrier gas mixing with the hydrogen to form a mixture, and (6) analyzing the mixture.

In another embodiment, the disclosed measuring system may include (1) a thermal desorption chamber, (2) a vacuum pump in selective fluid communication with the thermal desorption chamber, (3) a heating element received in the thermal desorption chamber, (4) a carrier gas source in selective fluid communication with the thermal desorption chamber, and (5) a detector in selective fluid communication with the thermal desorption chamber.

In yet another embodiment, the disclosed measuring system may include (1) a thermal desorption chamber, (2) a vacuum pump in selective fluid communication with the thermal desorption chamber, the vacuum pump being configured to draw a vacuum in the thermal desorption chamber, (3) a heating element received in the thermal desorption chamber, the heating element being configured to heat a sample housed in the thermal desorption chamber to desorb hydrogen from the sample, (4) a detector in selective fluid communication with the thermal desorption chamber, and (5) a carrier gas source in selective fluid communication with the thermal desorption chamber to carry the desorbed hydrogen to the detector.

Other embodiments of the disclosed system and method for detecting hydrogen content in a sample (or the content of other target species in a sample) will become apparent from the following detailed description, the accompanying drawings and the appended claims.

DETAILED DESCRIPTION

Disclosed are systems and methods for detecting the hydrogen content of a sample. The sample may be a sample of a structural material, such as high-strength steel or a titanium alloy. Optionally, the sample may have been chemically treated or plated with a corrosion-resistant coating material, such as a titanium-cadmium coating or a zinc-nickel coating, using, for example, an electroplating process. Therefore, it may be desirable to know the amount of hydrogen, such as diffusible hydrogen, within the sample and, thus, the hydrogen embrittlement potential of the sample.

While reference is made herein to the detection of hydrogen content in a sample, it is also contemplated that the disclosed systems and methods may be used to detect the presence and/or the concentration of other species within a sample. Furthermore, while reference is made herein to hydrogen embrittlement potential, the disclosed systems and methods may be used to detect the content of hydrogen (or other species) for a variety of reasons, not just for determining hydrogen embrittlement potential.

Figure 1:
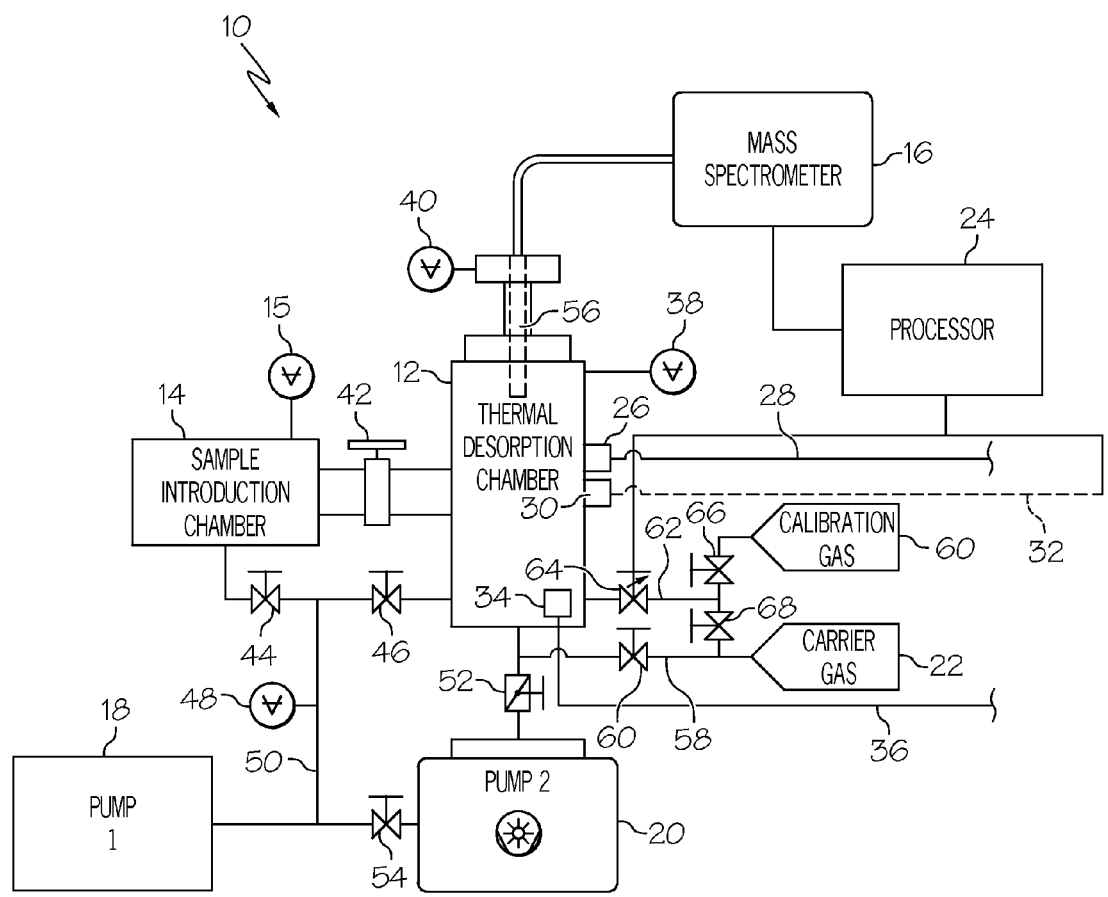
FIG. 1 is a schematic diagram depicting one embodiment of the disclosed system for detecting hydrogen content in a sample.

Referring to FIG. 1, one embodiment of the disclosed system for detecting hydrogen content in a sample, generally designated 10, may include a thermal desorption chamber 12, a sample introduction chamber 14, a detector 16, a first vacuum pump 18, a second vacuum pump 20 and a carrier gas source 22. An optional processor 24 may also be provided to operate the system 10, monitor temperature and pressure, and receive and process data from the detector 16.

Thus, a sample may be introduced to the thermal desorption chamber 12, such as by way of the sample introduction chamber 14, such that the sample may be heated to desorb hydrogen from the sample. The carrier gas source 22 may supply a carrier gas to the thermal desorption chamber 12 to carry the desorbed hydrogen to the detector 16 where the desorbed hydrogen may be measured. Background hydrogen, which may compromise the measurements taken at the detector 16, may be minimized by evacuating the thermal desorption chamber 12 and the sample introduction chamber 14 using the pumps 18, 20 prior to introducing the sample to the thermal desorption chamber 12.

The thermal desorption chamber 12 may be a rigid, heat-resistant enclosure capable of maintaining a vacuum (i.e., substantially gas-tight). For example, the thermal desorption chamber 12 may be a vessel constructed to withstand internal pressures of $10^{-8}$ Torr or lower. However, thermal desorption chambers 12 configured to operate at higher pressures (e.g., $10^{-7}$ Torr, $10^{-6}$ Torr, $10^{-5}$ Torr, $10^{-4}$ Torr, $10^{-3}$ Torr, $10^{-2}$ Torr or higher) may be used without departing from the scope of the present disclosure.

The size of the thermal desorption chamber 12 may be dictated by, among other things, the maximum sample size intended to be evaluated using the disclosed system 10. For example, the thermal desorption chamber 12 may be sufficiently large to receive the same sample required for the ASTM F519 test method. Therefore, using the same samples, correlations may be made between the results of the ASTM F519 test method and the measurements obtained using the disclosed system 10.

The thermal desorption chamber 12 may be constructed from a heat-resistant and substantially rigid material that is capable of withstanding vacuum pressures. Examples of suitable materials for constructing the thermal desorption chamber 12 include metals, such as steel (e.g., mild or stainless), brass and aluminum, and non-metals, such as ceramic materials, composite materials and polymeric materials.

It is noted that aluminum has roughly seven orders of magnitude less hydrogen than stainless steel. Therefore, without being limited to any particular theory, it is believed that constructing the thermal desorption chamber 12 from low hydrogen aluminum may contribute to a reduction in background hydrogen and, thus, improve overall performance of the disclosed system 10. A suitable aluminum thermal desorption chamber 12, or at least the components thereof, may be obtained from Atlas Technologies of Port Townsend, Wash.

A heating element 26 may be provided to heat the thermal desorption chamber 12 (or at least the sample housed within the thermal desorption chamber 12) to desorb hydrogen from the sample. For example, the heating element 26 may include one or more heating lamps (e.g., a halogen heating lamp), and the heating lamps may be supplied with electrical energy by way of an electrical power line 28. While use of a heat lamp is specifically disclosed, those skilled in the art will appreciate that various heating elements 26 (e.g., heating cartridges) may be used to heat the sample within the thermal desorption chamber 12 without departing from the scope of the present disclosure.

A temperature sensor 30, such as a thermocouple, may be provided to detect the heat generated within the thermal desorption chamber 12. The temperature sensor 30 may be in communication with the processor 24 by way of communication line 32. Therefore, the processor 24 may control the heating element 26 to heat the sample within the thermal desorption chamber 12 to the desired temperature (e.g., at least 150° C.) based on temperature signals received from the temperature sensor 30.

Optionally, an ultraviolet lamp 34 may be provided within the thermal desorption chamber 12. The ultraviolet lamp 34 may be supplied with electrical energy by way of an electrical power line 36, and may emit light having a wavelength ranging from about 200 to about 400 nanometers.

Without being limited to any particular theory, it is believed the ultraviolet light may excite water molecules (a background hydrogen source), thereby preventing the water molecules from attaching to the walls of the thermal desorption chamber 12. Therefore, the ultraviolet lamp 34 may be actuated when the thermal desorption chamber 12 is being purged to minimize background hydrogen, as discussed in greater detail herein.

Vacuum gauges 38, 40 may be coupled to the thermal desorption chamber 12 to monitor the pressure within the thermal desorption chamber 12. For example, vacuum gauge 38 may be an ion gauge configured to measure pressures between $10^{-4}$ and $10^{-10}$ Torr, while vacuum gauge 40 may be a thermocouple gauge configured to measure pressures between about 1 atm and $10^{-4}$ Torr. The vacuum gauges 38, 40 may optionally be in communication with the processor 24 such that the processor 24 may control the pressure within the thermal desorption chamber 12.

The sample introduction chamber 14 may be a load lock chamber selectively coupled to the thermal desorption chamber 12. Therefore, the sample introduction chamber 14 may be a rigid enclosure capable of maintaining a vacuum (e.g., pressures of $10^{-4}$ Torr or lower), and may be sized and shaped to receive the sample.

A vacuum gauge 15 may be coupled to the sample introduction chamber 14 to monitor the pressure within the sample introduction chamber 14. For example, the vacuum gauge 15 may be a thermocouple gauge configured to measure pressures between about 1 atm and $10^{-4}$ Torr. The vacuum gauge 15 may optionally be in communication with the processor 24 such that the processor 24 may control the pressure within the sample introduction chamber 14.

When the sample introduction chamber 14 is used, the sample may first be introduced to the sample introduction chamber 14 and a vacuum may be drawn on the sample introduction chamber 14. Then, the sample introduction chamber 14 may be fluidly coupled with the thermal desorption chamber 12 (e.g., by way of valve 42) such that the sample may be transferred to the thermal desorption chamber 12. For example, once the sample introduction chamber 14 is fluidly coupled to the thermal desorption chamber 12, a push rod (not shown) or the like may be used to transfer the sample from the sample introduction chamber 14 to the thermal desorption chamber 12.

Thus, use of the sample introduction chamber 14 to introduce the sample to the thermal desorption chamber 12, rather than directly introducing the sample to the thermal desorption chamber 12, may minimize the amount of ambient air (a background hydrogen source) introduced to the thermal desorption chamber 12 during introduction of the sample to the thermal desorption chamber 12.

The first vacuum pump 18 may be selectively coupled to both the thermal desorption chamber 12 and the sample introduction chamber 14 by way of valves 44, 46. Therefore, by selectively opening and closing the valves 44, 46, the first vacuum pump 18 may be actuated to draw a vacuum in either the thermal desorption chamber 12 or the sample introduction chamber 14.

The first vacuum pump 18 may be a low vacuum pump, and may be used to draw an initial vacuum within the thermal desorption chamber 12 and the sample introduction chamber 14. In one particular implementation, the first vacuum pump 18 may be capable of drawing a vacuum of at least about $10^{-3}$ Torr in both the thermal desorption chamber 12 and the sample introduction chamber 14.

As an example, the first vacuum pump 18 may be a mechanically-actuated positive displacement pump. Since oil may be a background hydrogen source, the first vacuum pump 18 may optionally be an oil-free pump, such as a diaphragm, peristaltic or scroll pump.

A vacuum gauge 48 may be mounted on the fluid line 50 that couples the first vacuum pump 18 with the sample introduction chamber 14 and the thermal desorption chamber 12 to monitor the vacuum created by the first vacuum pump 18. For example, the vacuum gauge 48 may be a thermocouple gauge configured to measure pressures between about 1 atm and $10^{-4}$ Torr. The vacuum gauge 48 may optionally be in communication with the processor 24 such that the processor 24 may control the vacuum generated by the first vacuum pump 18.

The second vacuum pump 20 may be selectively coupled to the thermal desorption chamber 12 by way of valve 52, and may be connected in series between the first vacuum pump 18 and the thermal desorption chamber 12. Valve 54 may be positioned between the second vacuum pump 20 and the first vacuum pump 18. Therefore, with valves 52, 54 open, the second vacuum pump 20 may be actuated, either alone or in combination with the first vacuum pump 18, to draw a vacuum in the thermal desorption chamber 12.

The second vacuum pump 20 may be a high vacuum pump, and may be used to draw high vacuum within the thermal desorption chamber 12. In one particular implementation, the second vacuum pump 20 may be capable of drawing a vacuum of at least about $10^{-9}$ Torr in the thermal desorption chamber 12.

As an example, the second vacuum pump 20 may be a high vacuum cryopump or a turbomolecular pump, both of which generally do not produce background hydrogen (or hydrogen-containing compounds). However, other high vacuum pumps may also be used without departing from the scope of the present disclosure.

Thus, the first vacuum pump 18 may be actuated to draw a vacuum within the sample introduction chamber 14 after the sample has been placed into the sample introduction chamber 14, thereby minimizing the amount of ambient air that will be introduced to the thermal desorption chamber 12 with the sample. The first and second vacuum pumps 18, 20 may be actuated to draw a high vacuum within the thermal desorption chamber 12, thereby significantly minimizing the amount of background hydrogen (or hydrogen-containing compounds) within the thermal desorption chamber 12.

The detector 16 may be any analytical apparatus or system capable of measuring the content of a target species (e.g., hydrogen) within the thermal desorption chamber 12. The detector 16 may include a sampling probe 56 that extends into the thermal desorption chamber 12 to couple the detector 16 with the thermal desorption chamber 12, particularly with the gaseous fluid within the thermal desorption chamber 12.

The detector 16 may be a mass spectrometer. Since the target species (e.g., hydrogen) will be carried to the detector 16 in a carrier gas, the mass spectrometer may be capable of sampling under system conditions, such as at elevated temperatures and within the viscous flow regime (i.e., not high vacuum).

In one particular construction, the detector 16 may be an atmospheric ionization mass spectrometer (i.e., a mass spectrometer capable of sampling at atmospheric pressure). One example of suitable atmospheric ionization mass spectrometer is the HPR-20 QIC TMS gas analyzer, commercially available from Hiden Analytical Ltd. of Warrington, England.

In one variation, the detector 16 may be a mass spectrometer capable of sample at pressures above $10^{-4}$ Torr. In another variation, the detector 16 may be a mass spectrometer capable of sample at pressures above $10^{-3}$ Torr. In yet another variation, the detector 16 may be a mass spectrometer capable of sample at pressures above $10^{-2}$ Torr.

The carrier gas source 22 may be a source of carrier gas, and may be fluidly coupled with the thermal desorption chamber 12 by way of fluid line 58. A valve 60 may be provided to control the flow of the carrier gas from the carrier gas source 22 to the thermal desorption chamber 12.

The carrier gas may be an inert gas or a mixture of inert gasses. For example, the carrier gas may be argon or helium, though other gases, including other inert gases, may be used as the carrier gas without departing from the scope of the present disclosure. Without being limited to any particular theory, the selection of a carrier gas that is substantially free of hydrogen, whether free hydrogen or hydrogen compounded with other elements, may result in significantly more accurate measurements.

Optionally, the system 10 may also include a calibration gas source 60 fluidly coupled with the thermal desorption chamber 12 by way of fluid line 62. The calibration gas source 60 may include a calibration gas having a known concentration of the target species (e.g., hydrogen) in a carrier gas (e.g., argon).

Thus, by selectively opening/closing valves 64, 66, 68, the calibration gas may be passed from the calibration gas source 60 to the thermal desorption chamber 12 by way of fluid line 62. From the thermal desorption chamber 12, the calibration gas may pass to the sampling probe 56 such that it may be analyzed by the detector 16, thereby facilitating calibration of the detector 16.

Accordingly, the disclosed system 10 may be used to detect the content of hydrogen (or other species) in a sample. The first and second pumps 18, 20, as well as the ultraviolet lamp 34, may be employed to minimize background hydrogen within the thermal desorption chamber 12. The sample introduction chamber 14 may be used to introduce a sample to the thermal desorption chamber 12 without introducing a significant amount of ambient air (a background hydrogen source). The sample placed in the thermal desorption chamber 12 may be heated by the heating element 26 to desorb hydrogen from the sample. The carrier gas source 22 may supply a carrier gas (e.g., argon) to the thermal desorption chamber 12 to transport the desorbed hydrogen to the detector 16. The detector 16, which may be a mass spectrometer, may measure the amount of desorbed hydrogen in the carrier gas stream.

Figure 2:
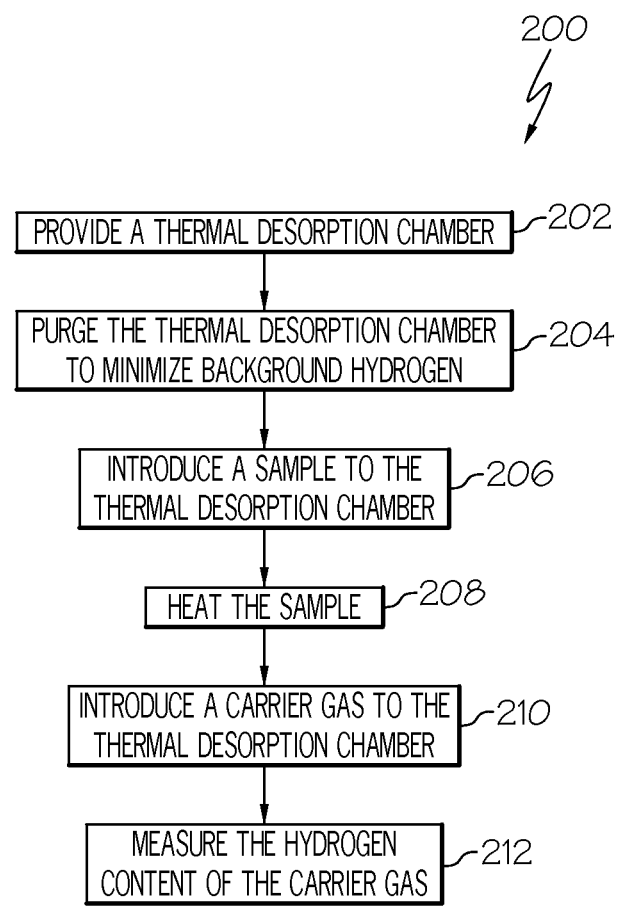
FIG. 2 is a flow chart depicting one embodiment of the disclosed method for detecting hydrogen content in a sample.

Referring to FIG. 2, also disclosed is a method, generally designated 200, for detecting hydrogen content in a sample. However, the disclosed method 200 may also be used for detecting the content of species other than hydrogen in a sample without departing from the scope of the present disclosure.

At step 202, the method 200 may begin with the step of providing a thermal desorption chamber. For example, the thermal desorption chamber may be the thermal desorption chamber 12 (FIG. 1) described in greater detail above.

At step 204, the thermal desorption chamber may be purged to minimize background hydrogen. The purging step may include drawing a high vacuum within the thermal desorption chamber to reduce to a minimum any background hydrogen within the thermal desorption chamber. Optionally, ultraviolet light may be emitted within the thermal desorption chamber (e.g., by way of ultraviolet lamp 34 shown in FIG. 1)

to detach any hydrogen or hydrogen-containing compounds (e.g., water) from the walls of the thermal desorption chamber.

At this point, those skilled in the art will appreciate that minimizing background hydrogen within the thermal desorption chamber during the purging step 204 may result in more accurate measurements of the hydrogen content within the sample. Therefore, the purging step 204 may be limited by cost considerations. Nonetheless, in one particular implementation of the disclosed method 200, the purging step 204 may reduce background hydrogen down to at most about 10 parts per million, such as at most about 1 part per million or at most about 10 parts per billion.

At step 206, a sample may be introduced to the thermal desorption chamber. For example, the sample may be a piece of high-strength structural material, such as high-strength steel. Optionally, the sample may be plated, such as with a titanium-cadmium coating or a zinc-nickel coating.

The introducing step 206 is shown in FIG. 2 being performed after the purging step 204. For example, the thermal desorption chamber may be purged, and the sample may be introduced to the purged thermal desorption chamber by way of a sample introduction chamber (e.g., chamber 14 in FIG. 1). However, the purging step 204 may be performed after the introducing step 206, or both before and after the introducing step 206, without departing from the scope of the present disclosure.

At step 208, the sample within the thermal desorption chamber may be heated, thereby desorbing hydrogen from the sample. For example, the heating step 208 may be performed by actuating a heating element 26 (FIG. 1) within the thermal desorption chamber.

At step 210, a carrier gas (e.g., argon) may be introduced to the thermal desorption chamber to mix with any hydrogen that desorbs from the sample. The carrier gas may increase the pressure within the thermal desorption chamber, thereby allowing flow (e.g., creating a viscous flow regime) within the thermal desorption chamber. For example, the flowing carrier gas may increase the pressure within the thermal desorption chamber to about $10^{-2}$ Torr or above. Therefore, the carrier gas may carry to the detector (detector 16 in FIG. 1) any hydrogen that desorbs from the sample.

At step 212, the hydrogen content of the desorbed hydrogen-carrier gas mixture may be measured. For example, the measuring step 212 may be performed by a mass spectrometer, thereby providing an actual measurement of hydrogen content.

Accordingly, the disclosed method 200 may be used to obtain a direct measurement of hydrogen (or other species) within a sample.

Figure 3:
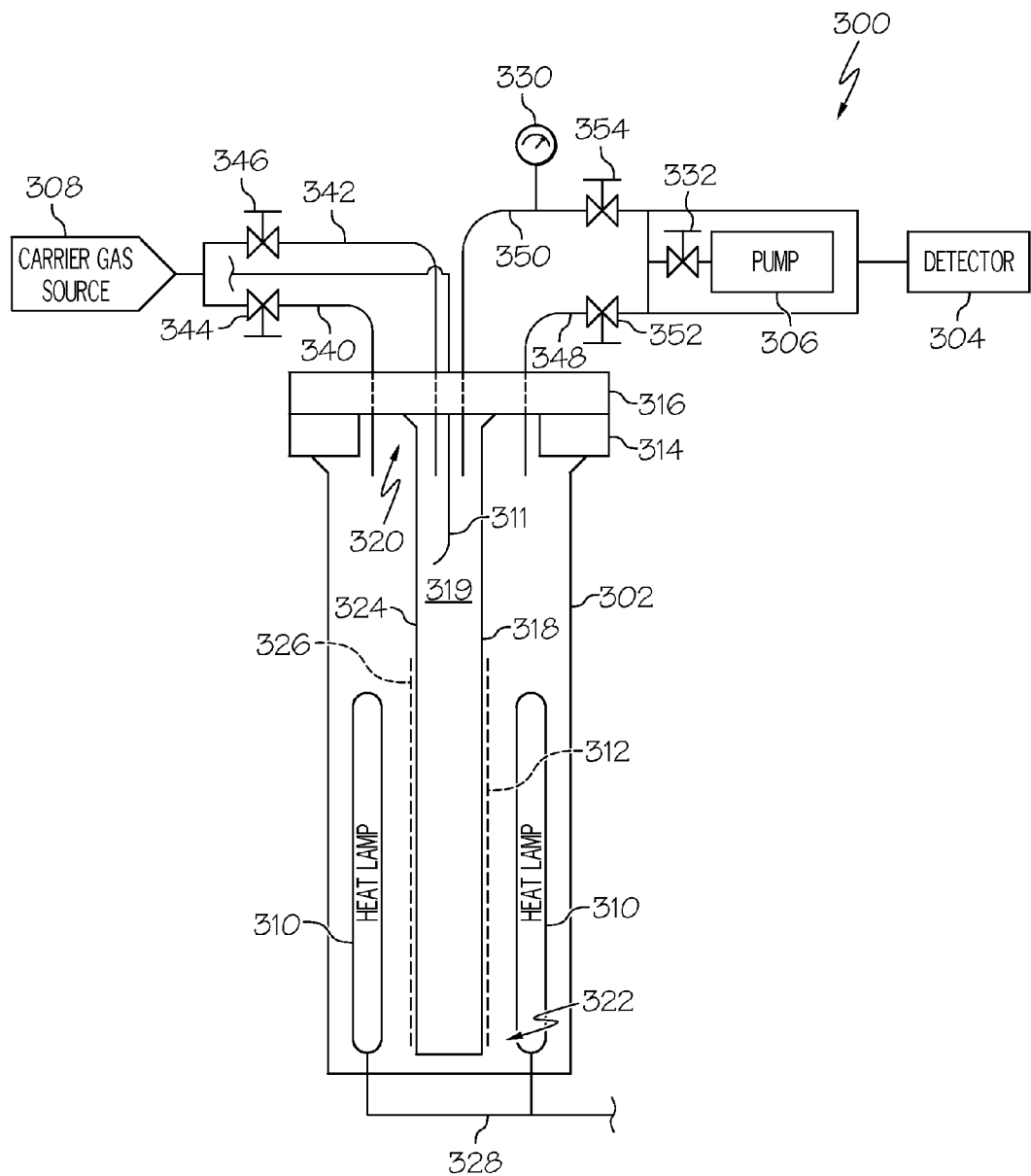
FIG. 3 is a schematic diagram depicting an alternative embodiment of the disclosed system for detecting hydrogen content in a sample.

Referring to FIG. 3, one alternative embodiment of the disclosed system for detecting hydrogen content in a sample, generally designated 300, may include a thermal desorption chamber 302, a detector 304, a vacuum pump 306, a carrier gas source 308 and one or more heating elements 310. A sample probe 312 may be enclosed within the thermal desorption chamber 302.

The thermal desorption chamber 302 may be a rigid, heat-resistant enclosure capable of maintaining a vacuum. For example, the thermal desorption chamber 302 may be constructed from low hydrogen aluminum. The thermal desorption chamber 302 may be sized and shaped to receive the sample probe 312 therein.

The thermal desorption chamber 302 may include a sealing flange 314 and a sealing plate 316 sealingly connected to the sealing flange 314 to enclose the thermal desorption chamber 302. Through-holes may be formed in the sealing plate 316 to facilitate coupling the thermal desorption chamber 302 with the detector 304, the vacuum pump 306 and the carrier gas source 308, while maintaining the thermal desorption chamber 302 as a substantially gas-tight enclosure.

The sample probe 312 may be connected to the sealing plate 316 and enclosed within the thermal desorption chamber 302.

In one particular expression, the sample probe 312 may include a hollow tubular body 318 that defines an internal bore 319, and that includes a first end 320 connected to the sealing plate 316 and a sealed (e.g., capped) second end 322. For example, the sample probe 312 may be a length of 4130 stainless steel tubing (e.g., 0.5 inch diameter), similar to the immersion probe used in the ASTM F326 standard test for the electronic measurement of hydrogen embrittlement potential resulting from cadmium electroplating processes, and may be used to test other chemical processes.

Optionally, at least a portion of the outer surface 324 of the body 318 of the sample probe 312 may include plating 326. For example, the plating 326 may be a titanium-cadmium material or a zinc-nickel material. Those skilled in the art will appreciate that hydrogen may desorb from both the sample probe 312 and the plating 326. Therefore, the sample probe 312 and/or the plating 326 may be the sample analyzed by the system 300.

The heating elements 310 may be enclosed within the thermal desorption chamber 302, and may be arranged to heat the sample probe 312 to desorb hydrogen from the sample probe 312. For example, the heating elements 310 may be heating lamps, such as halogen heating lamps, and the heating lamps may be supplied with electrical energy by way of an electrical power line 328.

A temperature sensor 311, such as a thermocouple, may be provided to detect the heat generated by the heating elements 310 within the thermal desorption chamber 302. Therefore, the temperature of the sample probe 312 may be controlled by controlling the heating elements 310 based on signals received from the temperature sensor 211.

The vacuum pump 306 may be selectively coupled to the thermal desorption chamber 302 by way of a valve 332. The vacuum pump 306 may be actuated to draw a vacuum in the thermal desorption chamber 302.

Optionally, a vacuum gauge 330 may be coupled to the thermal desorption chamber 302 (or one of the fluid lines in communication with the thermal desorption chamber 302) to monitor the pressure within the thermal desorption chamber 302. Therefore, the pressure within the thermal desorption chamber 302 may be controlled by controlling the vacuum pump 306 based on signals received from the vacuum gauge 330.

Thus, the vacuum pump 306 may be actuated to draw a vacuum within the thermal desorption chamber 302, thereby significantly minimizing the amount of background hydrogen within the thermal desorption chamber 302.

The carrier gas source 308 may be a source of a carrier gas, such as argon, and may be fluidly coupled with the thermal desorption chamber 302. A first fluid line 340 may feed the carrier gas into the thermal desorption chamber 302 outside of the sample probe 312 and a second fluid line 342 may feed the carrier gas into the internal bore 319 of the sample probe 312. Therefore, the carrier gas may be used to sample hydrogen desorbed externally to the sample probe 312 and/or desorbed hydrogen that diffused into the sample probe 312. The flow of carrier gas from the carrier gas source 308 through the fluid lines 340, 342 may be controlled by valves 344, 346.

The detector 304, which may be a mass spectrometer, as discussed above, may be in fluid communication with the thermal desorption chamber 302. A first fluid line 348 may couple the detector 304 with the thermal desorption chamber 302 outside of the sample probe 312 and a second fluid line 350 may couple the detector 304 with the internal bore 319 of the sample probe 312.

Thus, the carrier gas may pass from the carrier gas source 308 into the thermal desorption chamber 302 where it may mix with any hydrogen desorbed from the sample probe 312. The resulting desorbed hydrogen-carrier gas mixture may flow to the detector 304 by way of fluid lines 348, 350. The flow of the desorbed hydrogen-carrier gas mixture to the detector 304 may be controlled by valves 352, 354.

Accordingly, the disclosed system 300 may be used to detect the content of hydrogen (or other species) in the sample probe 312. Absolute measurements of hydrogen (or other species) content may be obtained. Furthermore, since the sample probe 312 may also be the immersion probe used in the ASTM F326 standard test for the electronic measurement of hydrogen embrittlement potential resulting from cadmium electroplating processes, two different analyses (e.g., the disclosed method and the ASTM F326 standard test method) may be performed on the same sample probe, thereby allowing for correlation between results (e.g., determining the absolute quantity of hydrogen that corresponds to a failure in the ASTM F326 standard test method).

Although various embodiments of the disclosed system and method for detecting hydrogen content in a sample have been shown and described, modifications may occur to those skilled in the art upon reading the specification. The present application includes such modifications and is limited only by the scope of the claims.

What is claimed is:

1. A measuring method comprising the steps of:
    drawing a vacuum in a chamber;
    placing a sample probe into said chamber, said sample probe defining an internal bore, wherein said internal bore is fluidly isolated from said chamber outside of said sample probe;
    heating said sample probe to desorb a target species from said sample probe;
    feeding a carrier gas into said chamber outside of said sample probe by way of a first fluid line, wherein said carrier gas mixes with said desorbed target species in said chamber to form a first mixture;
    feeding said carrier gas into said internal bore by way of a second fluid line, wherein said carrier gas mixes with said desorbed target species in said internal bore to form a second mixture;
    passing said first mixture and said second mixture to a detector; and
    analyzing said first mixture and said second mixture.

2. The method of claim 1 wherein said chamber is formed from aluminum.

3. The method of claim 1 wherein said vacuum is at a pressure of at most $10^{-3}$ Torr.

4. The method of claim 1 wherein said vacuum is at a pressure of at most $10^{-6}$ Torr.

5. The method of claim 1 further comprising the step of exposing said chamber to ultraviolet light.

6. The method of claim 5 wherein said exposing step is performed during said drawing step.

7. The method of claim 1 wherein said drawing step is performed after said placing step.

8. The method of claim 1 wherein said heating step comprises heating said sample probe to a temperature of at least 70° C.

9. The method of claim 1 wherein said target species is hydrogen.

10. The method of claim 1 wherein said target species is diffusible hydrogen.

11. The method of claim 1 wherein said carrier gas comprises argon.

12. The method of claim 1 wherein said detector comprises a mass spectrometer, and wherein said analyzing step comprises quantifying said target species in said first mixture and said second mixture.

13. The method of claim 1 wherein said analyzing step comprises determining a concentration of said target species in said first mixture and said second mixture.

14. The method of claim 1 further comprising the step of performing a second, different analysis on said sample probe using a different test method.

15. The method of claim 14 wherein said different test method is an ASTM F326 standard test method.

16. The method of claim 14 further comprising the step of correlating results from said analyzing step with results from said different test method.

17. The method of claim 1 wherein said sample probe comprises plating.

18. The method of claim 17 wherein said plating comprises at least one of a titanium-cadmium material and a zinc-nickel material.

* * * * *